(12) United States Patent
Lamadon

(10) Patent No.: US 7,887,481 B2
(45) Date of Patent: Feb. 15, 2011

(54) MOUNTABLE TOP-LOADING SURGICAL RETRACTOR

(75) Inventor: Thomas Lamadon, Les Verrières-de-Joux (FR)

(73) Assignee: Greatbatch Medical S.A., Orvin (CH)

( * ) Notice: Subject to any disclaimer, the term of this patent is extended or adjusted under 35 U.S.C. 154(b) by 945 days.

(21) Appl. No.: 11/381,153

(22) Filed: May 2, 2006

(65) Prior Publication Data

US 2007/0225743 A1 Sep. 27, 2007

Related U.S. Application Data

(60) Provisional application No. 60/783,198, filed on Mar. 16, 2006.

(51) Int. Cl.
*A61B 1/32* (2006.01)

(52) U.S. Cl. .................. 600/230; 600/211; 600/201; 600/226; 600/227

(58) Field of Classification Search .................. 600/201, 600/211, 22, 226, 227, 230, 231; 606/59
See application file for complete search history.

(56) References Cited

U.S. PATENT DOCUMENTS

| 6,042,540 A * | 3/2000 | Johnston et al. ............. 600/213 |
| 6,277,069 B1 * | 8/2001 | Gray ........................... 600/234 |
| 6,368,271 B1 * | 4/2002 | Sharratt ....................... 600/228 |
| 6,663,563 B1 * | 12/2003 | Sharratt ....................... 600/228 |
| 2002/0152833 A1 * | 10/2002 | Phillips ........................ 74/575 |
| 2002/0193666 A1 * | 12/2002 | Sherts et al. ................ 600/231 |
| 2005/0119656 A1 * | 6/2005 | Ferrante et al. ............... 606/59 |
| 2007/0093696 A1 * | 4/2007 | Sharratt ....................... 600/235 |

FOREIGN PATENT DOCUMENTS

WO   WO 03065911 A1 *  8/2003

* cited by examiner

*Primary Examiner*—Eduardo C Robert
*Assistant Examiner*—David W Bates
(74) *Attorney, Agent, or Firm*—Michael F. Scalise

(57) ABSTRACT

A mountable, top-loading retractor device that is quickly and easily mountable to a surgical tool support frame. The device has two main sections a mount assembly for attaching to the support frame, and a top-loading retractor assembly pivotably linked to the mount assembly. The mount assembly has opposed upper and lower clamping jaws to a grip a section of the frame when the assembly is operated to set the clamping jaws. The retractor assembly includes a retractor mechanism having a separate arm receivable into the top surface of the retractor assembly and engageable by the retractor mechanism. The arm extends beyond the retractor assembly and is positionable along its length. The distal end of the arm is adapted to attach to a surgical retractor tool, and to apply a force to operate the tool.

33 Claims, 11 Drawing Sheets

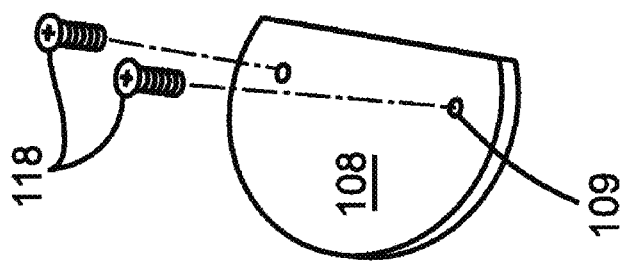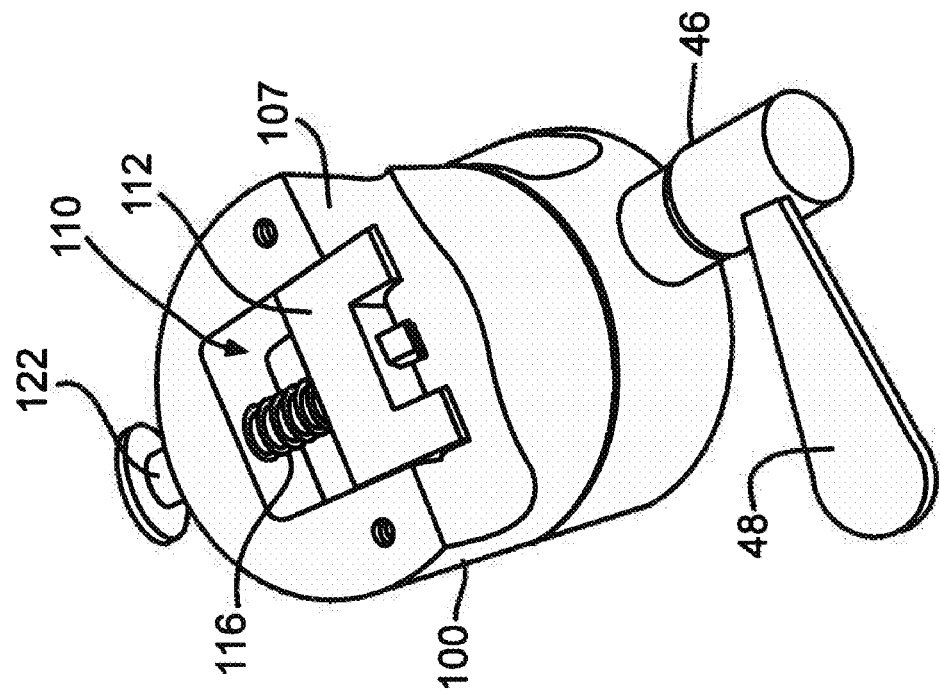
FIG. 3

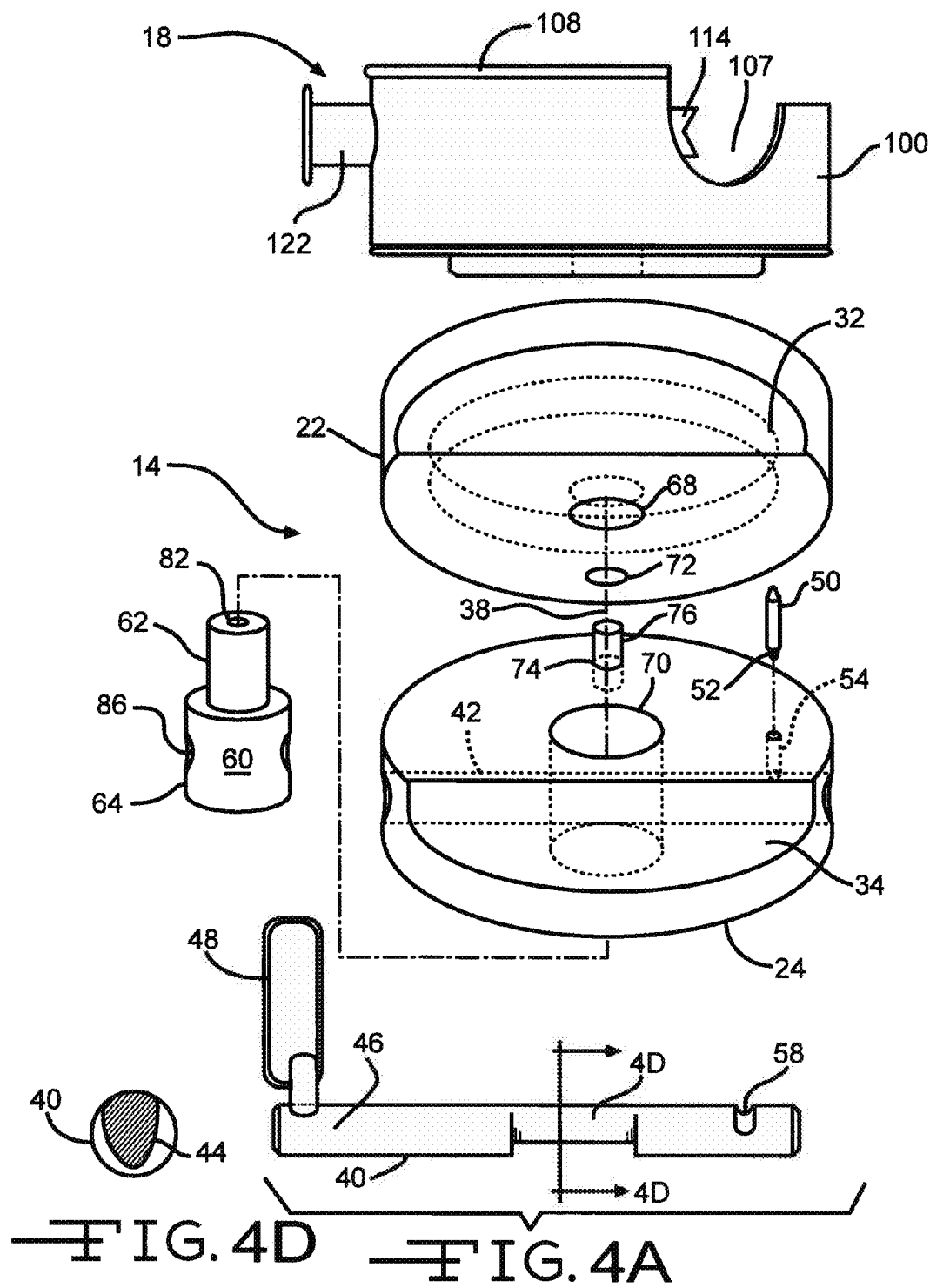

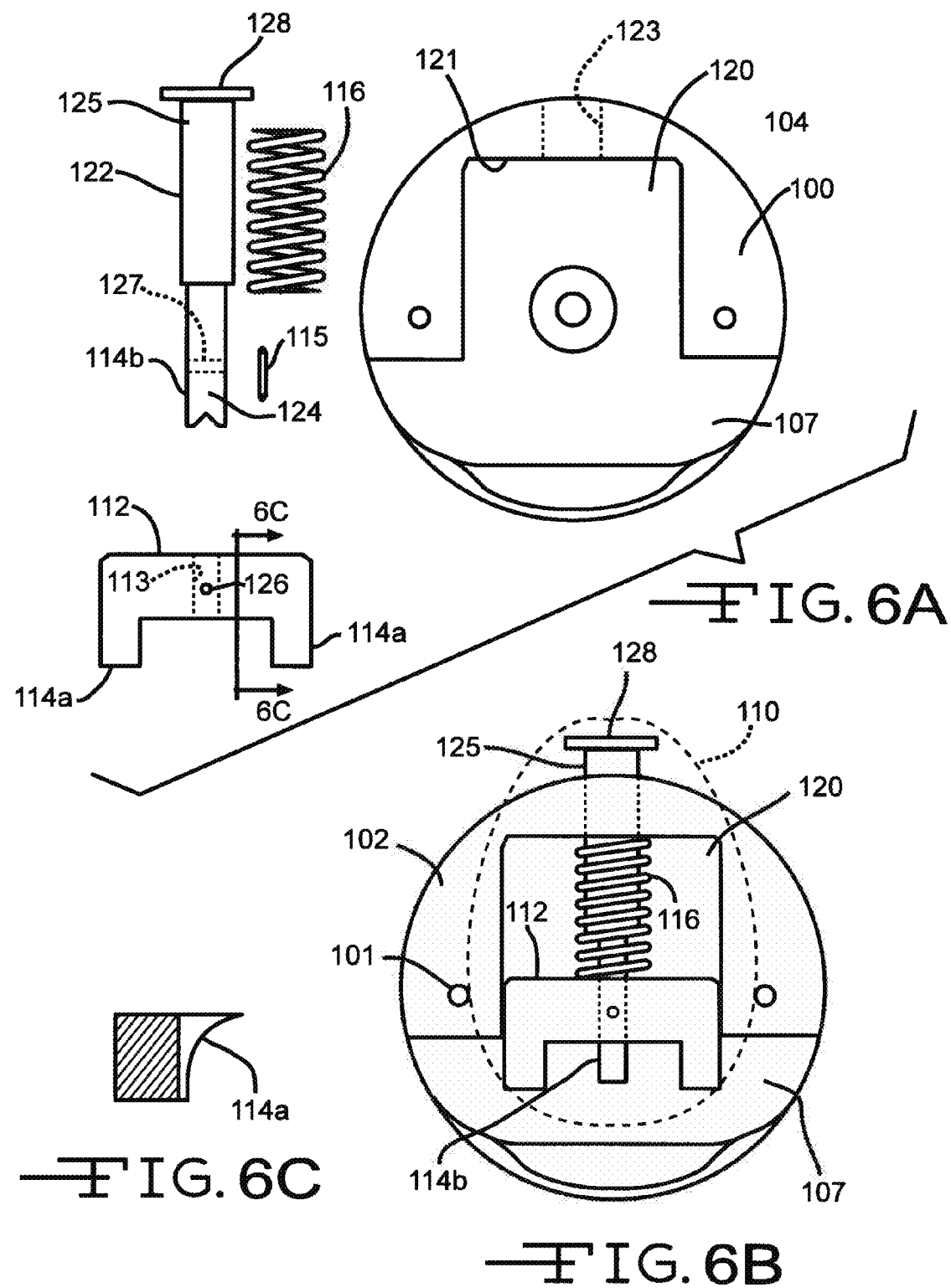

ized by like numbers with a different lower case letter
MOUNTABLE TOP-LOADING SURGICAL RETRACTOR The present application claims the benefit of prior filed U.S. Provisional Patent Application Ser. No. 60/783,198 filed 16 Mar. 2006, to which the present application is a regular U.S. national application.

FIELD OF THE INVENTION

This invention in the field of surgical devices. More specifically, the invention relates to mountable retractor devices for the retraction of soft tissue.

BACKGROUND OF THE INVENTION

Soft tissue retractor devices for surgical use are known in the field. Additionally, support frames (i.e., simple or complex networks of support rods) are used during surgical procedures to mount or support surgical devices during a procedure. The support frame provides a stable mounting and reference points for surgical tools and instruments. Because these support frames can sometimes be complex and can otherwise be in the way of the surgical team, it is important to have available mountable surgical devices which are quick and easy to mount. Further, the devices when mounted to the support frame are as minimally invasive into the work space of the surgical team as possible, and that the actions of mounting and operating the device be facile in a potentially space limited situation.

SUMMARY OF THE INVENTION

The present invention is a mountable, top-loading surgical retractor device. The present top-loading retractor device is quickly and easily mountable to a support frame. Additionally, when the device is mounted to the support frame it minimally protrudes into the work space of the surgical team, and the actions of mounting the device, and loading and operating the device is easily accomplished in a space limited situation. The present top-loading retractor device comprise two main assemblies: a mount assembly and a top-loading retractor assembly. The mount assembly has opposed upper and lower clamping jaws disposed to receive and grip a mounting rod of a support frame. The mounting assembly has a lever actuated clamping mechanism in mechanical communication with the upper and lower clamping jaws. The clamping mechanism is easily operable to quickly set and release the clamping jaws of the device.

The top-loading retractor assembly is pivotably linked to the mount assembly and has a limited degree of rotation relative to the mount about a common axis. The retractor assembly includes a housing block having a top surface, side surfaces and a bottom surface. A retractor mechanism is disposed in the top surface of the housing block. A separate retractor arm is receivable into an arm engagement slot in the top surface of the retractor assembly. Within the slot, the retractor arm is engageable by the retractor mechanism. The retractor arm is relatively long and its length extends well beyond the side surfaces of the housing block. The retractor arm has a surface feature that mate with the retractor mechanism, and is positionable along its length in the engagement slot. Once engaged, the retractor arm is incrementally re-positionable unidirectionally along its length by manually drawing on the proximal end of the arm. The distal end of the retractor arm is adapted to attach to a surgical retractor tool.

BRIEF DESCRIPTION OF THE DRAWINGS

FIG. 3 is a photographic top view of the present invention showing the engagement mechanism of the retractor.

FIGS. 4A, 4B and 4C are partial perspective side views of the combination mount and top-loading tool retractor assembly of the present invention showing the lower mount section (exploded) and the upper top-loading retractor section.

FIG. 4D is a cross-sectional view along line 4D-4D of FIG. 4A.

FIGS. 6A and 6B are drawings of (A) the separate component parts of the retractor mechanism of the retractor assembly, and (B) the component parts of the retractor mechanism assembled in the retractor assembly housing.

FIG. 6C is a cross-sectional view along line 6C-6C of FIG. 6A.

DETAILED DESCRIPTION OF THE INVENTION

Figure 1A:
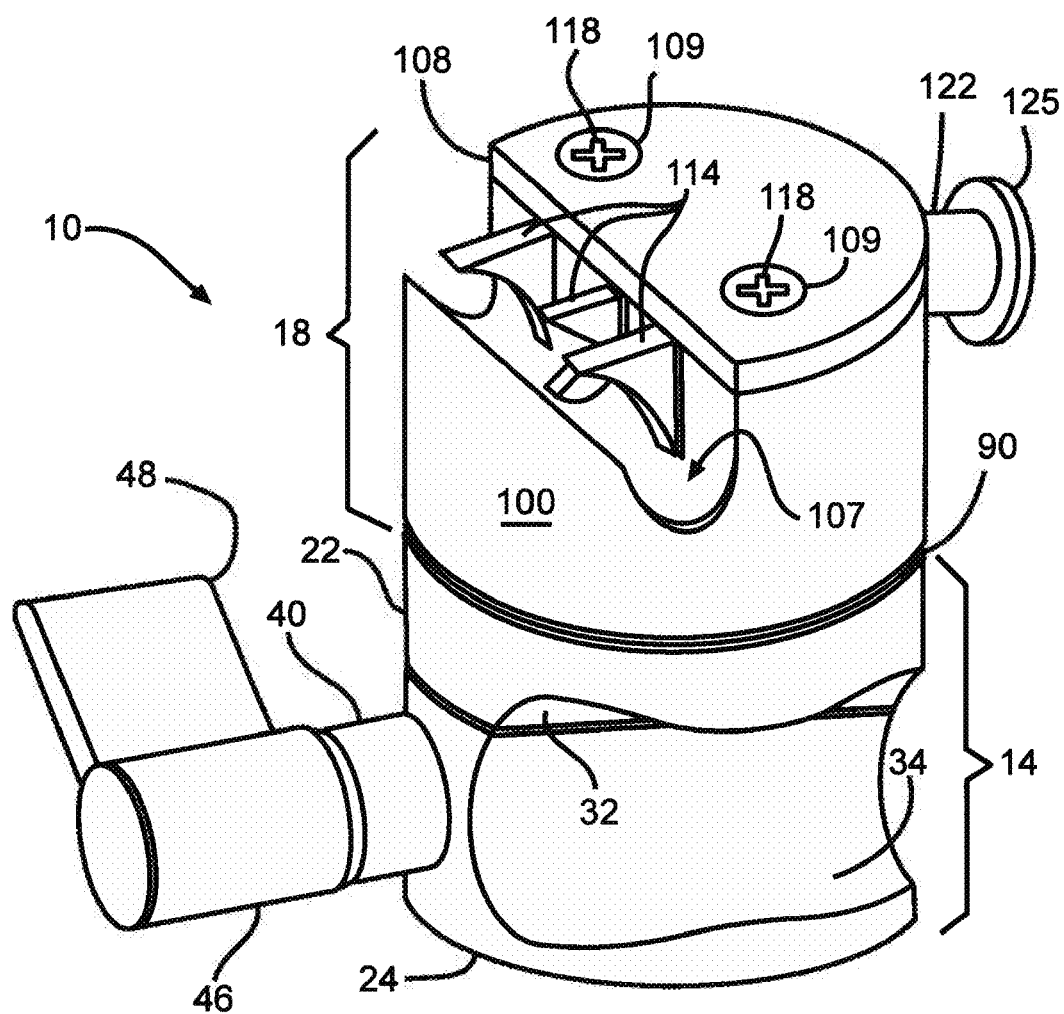
FIG. 1A is a perspective view of the present combination mount and top-loading tool retractor assembly disposed for mounting to a rod.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1B:
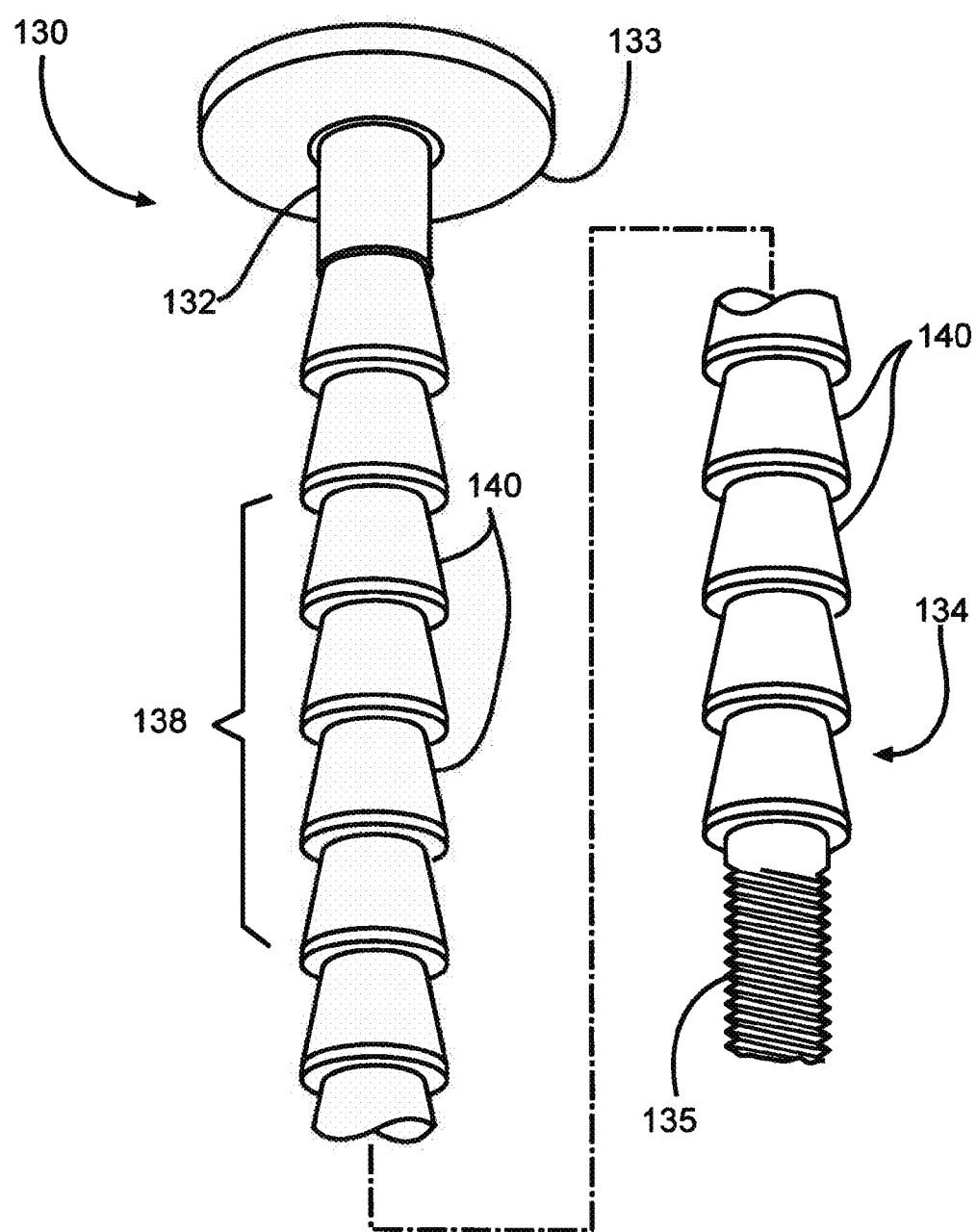
FIG. 1B is a top plan view of the draw/retractor arm of the present mountable top-loading surgical retractor.
Figure 7A:
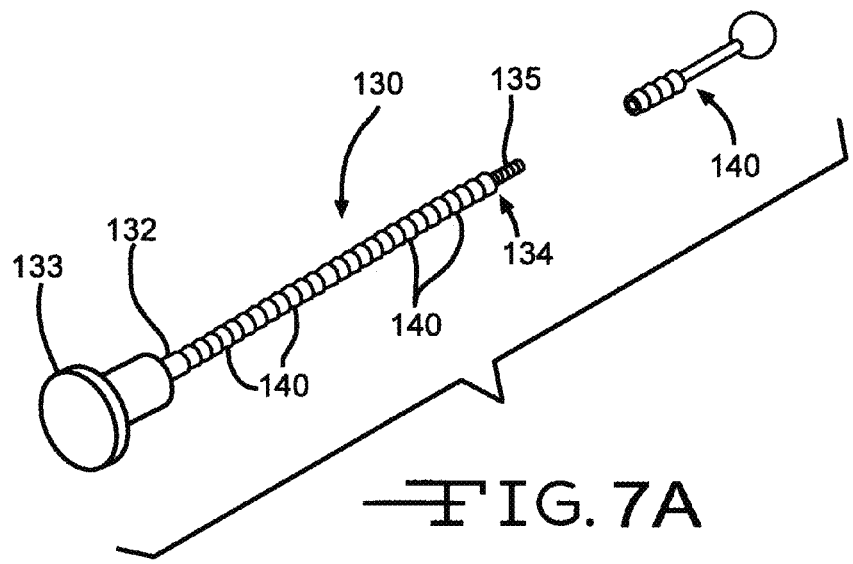
FIG. 7A is a perspective view of the retractor arm of the present invention.
Figure 7B:
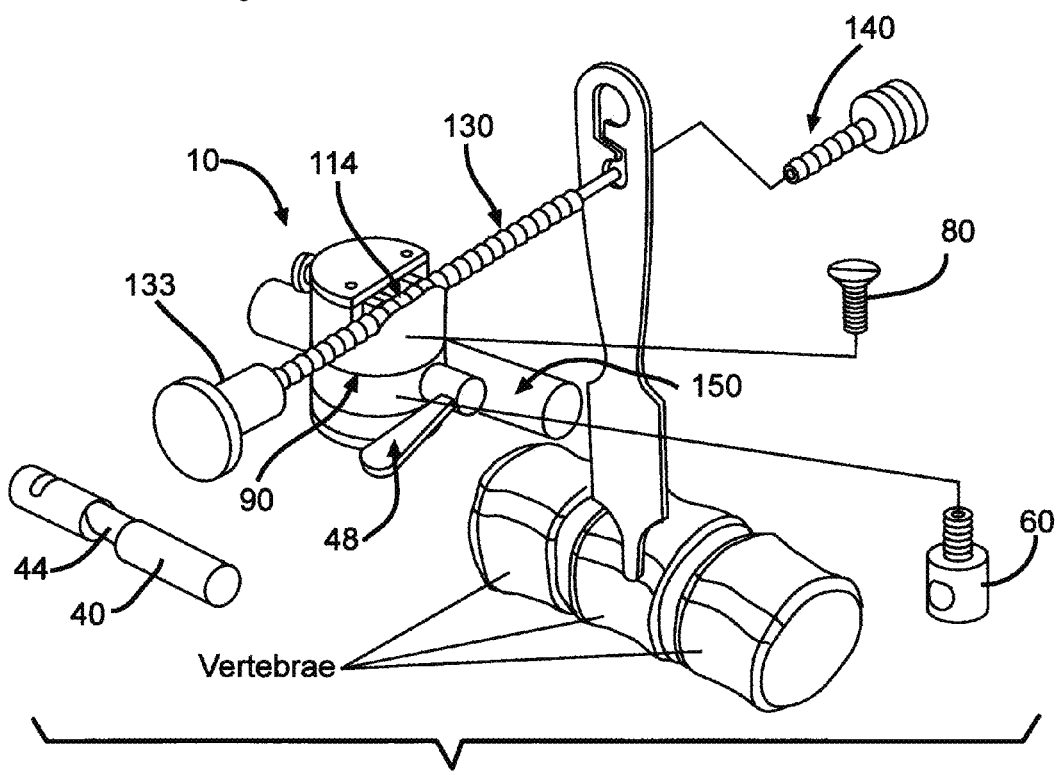
FIG. 7B is a perspective view of the present device mounted and in use.

As illustrated in FIG. 1, the present invention is a device that is easily and quickly mountable on an apparatus support rod, such as may be used at a surgical table to support various equipment and tools during a surgical procedure on a patient. Referring now to the figures, more specifically, the present invention is a mountable, top-loading surgical retractor device 10. The present device 10 is comprised of two main sections: a mounting assembly 14 and a top-loading retractor assembly 18. The mounting assembly 14 is disposed to enable the device 10 to be mounted to a support rod 150 (see FIG. 7B), as noted above. The retractor assembly has top-loading structural features to provide open access to the retractor mechanism of the device via the "top" of the device 10. A surgical procedure may require an environment crowded with equipment. The top loading feature allows the retractor arm 130 (see FIG. 1B) to be operated free of obstruction that a similar, but non-top loading device mount on the support rod might encounter in a crowded surgery environment.

The mount assembly 14 has an upper clamping jaw 22 disposed opposite a lower clamping jaw 24. The clamping jaws 22 and 24 are disposed to receive and grip a section of a support rod. A lever actuated clamping mechanism 28 (see FIG. 4B) is in mechanical communication with the upper and lower clamping jaws 22 and 24, and is operable to quickly set or release the clamping jaws. The top-loading retractor assembly 18 is pivotably linked to the mount assembly 14.

This means that the retractor assembly 18 and the mount assembly 14 are pivotable relative to each other about a common axis 38 of rotation when the mount assembly 14 is in a released condition. In the preferred embodiment of the figures, the degrees of rotation is was limited as disclosed below. Additionally, when the mount assembly 14 is in a set condition, the retractor assembly 18 is positionally fixed relative to the mount assembly 14. So, operation of the clamping mechanism 28 of the mount assembly 14 provides for setting the clamping jaws 22 & 24 and the rotational relationship of the two assemblies 14 and 18.

Figure 4B:
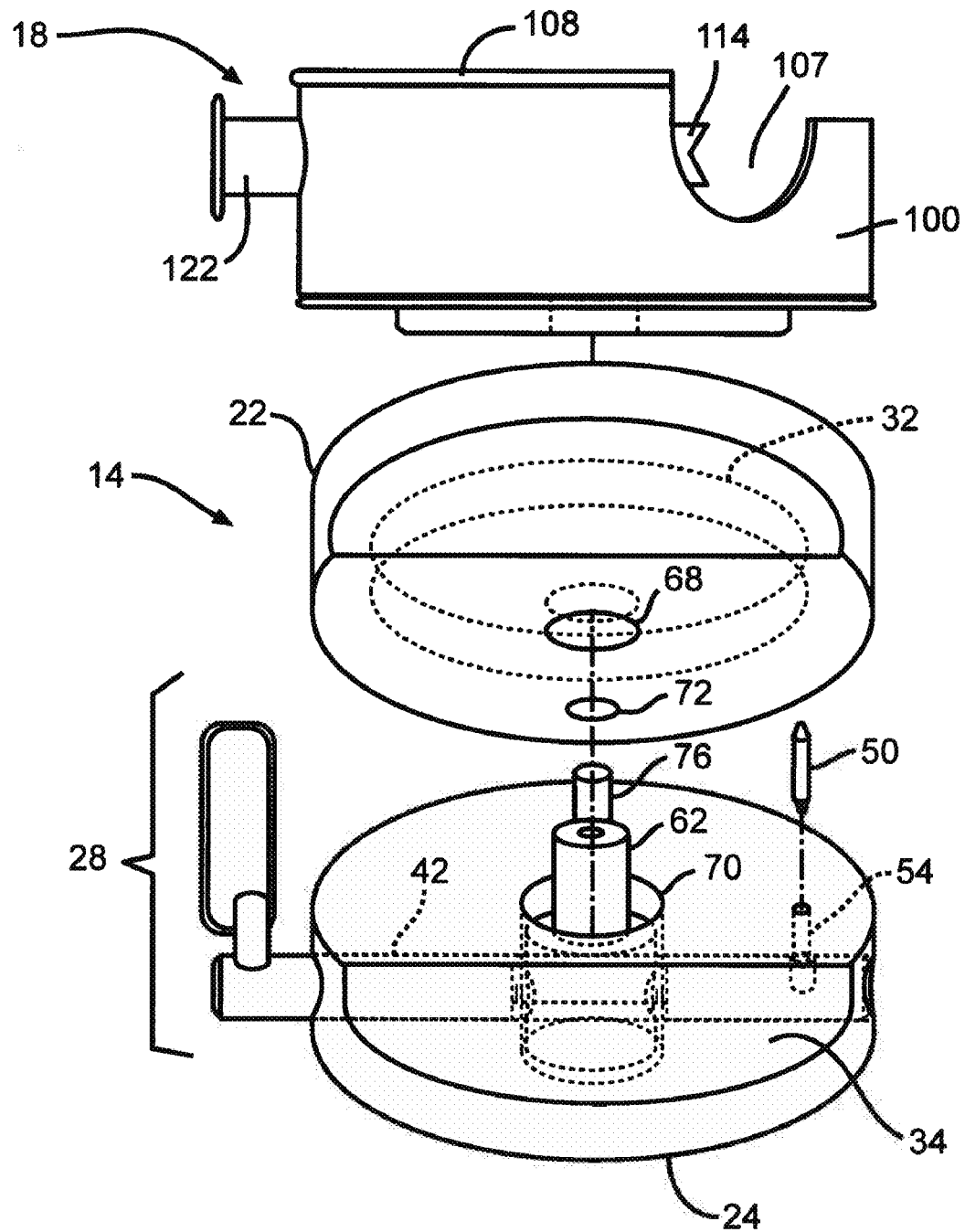
Figure 4C:
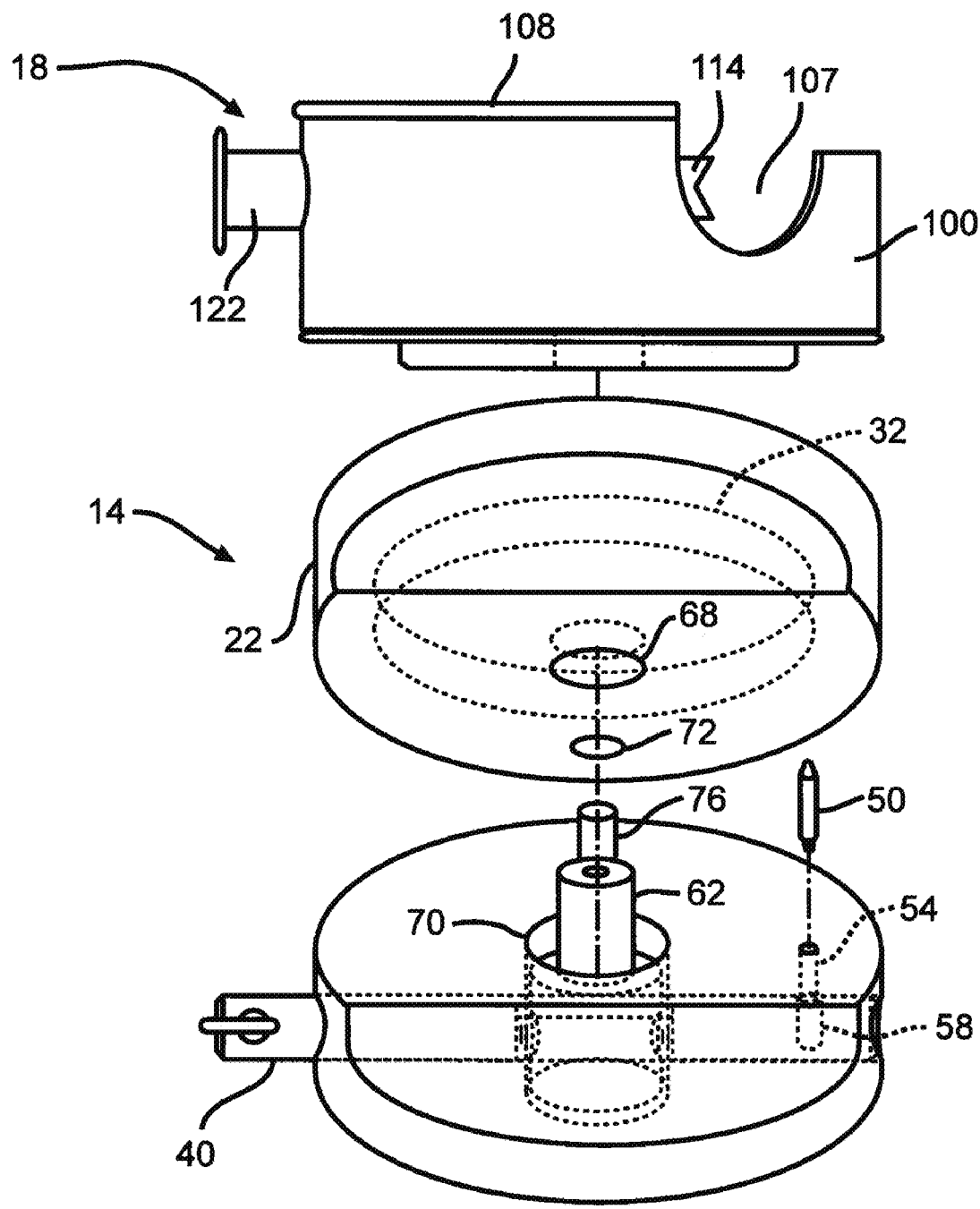

As illustrated in FIGS. 4A-4C, the opposed upper and lower clamping jaws 22 and 24 are configured with a similar cross-section. Additionally, each clamping jaw 22 and 24 is configured with a complementary portion 32 and 34 of a rod receiver 30 (see FIG. 2B). The complementary rod receiver portions 32 and 34 in combination are disposed to closely receive and grip a section of a support rod when the clamping mechanism 28 is operated to set the clamping jaws 22 and 24. The configurations of the rod receiver 30 are selectable by the ordinary skilled artisan depending on the configuration of the support rod and the weight the device 10 that is anticipated needing to be supported support.

The clamping mechanism 28 in the preferred embodiment illustrated is lever actuated. The clamping mechanism 28 comprised a cam shaft 40 which is rotatably received in a shaft passage 42 disposed in the lower clamping jaw 24. As illustrated in the FIG. 4A, the entire length of the shaft passage 42 passes completely through the lower clamping jaw 24, and the cam shaft 40 is received substantially in the full length of the passage 42. The cam shaft 40 has a lever end 46 extending from the shaft passage 42 external to the lower clamping jaw 24. A clamp lever 48 is configured to enable a user to apply a force to rotate the cam shaft 40 in the shaft passage 42. Although the clamp lever 48 is configured as in the illustrated embodiment, one of ordinary skill in the art can select a suitable easily operated lever means practicable in the present invention for manually rotating the cam shaft 40.

The cam shaft 40 is retained in the shaft passage by a shaft pin 50. The shaft pin 50 is received in and extends from a pin bore 54 disposed in the lower clamping jaw 24 and into the shaft passage 42. An end portion 52 of the shaft pin 50 extending from the pin bore 54 rides in a shaft stop channel 58 disposed in the cam shaft 40. The shaft pin 50 and stop channel 58 in combination provide for retaining the cam shaft 40 in the shaft passage 42, and for limiting the degree of rotation of the cam shaft 40. In the embodiment illustrated, the shaft pin 50 is held in the pin bore 54 by the upper clamping jaw 22 blocking one end of the pin bore 54. However, other means for retaining the shaft pin 50 in the pin bore 54 (e.g., by press fitting the pin 50 in the bore 54) are known to and practicable in the present invention by the ordinary skilled artisan. Also, the location of the pin 50, bore 54 and stop channel 58 combination, although illustrated as disposed at a cam shaft end distal from the lever end 46, may be reasonably practiced elsewhere along the cam shaft 40.

The upper clamping jaw 22 and the lower clamping jaw 24 are separate from each other. A clamping piston 60 links the two jaws together by closely passing through a piston bore disposed in each of the clamping jaws 22 and 24. In the embodiment illustrated, the clamping piston 60 is cylindrical and had an upper piston section 62 with a smaller radius than the lower piston section 64. The upper piston section 62 extends into the upper piston bore 68, and the lower piston section 64 extends into the lower piston bore 70.

The complementary portions 32 and 34 of the rod receiver 30 disposed in the opposed upper and lower clamping jaws 22 and 24, respectively, are kept in proper alignment with each other by a drift pin 76 received in corresponding drift holes 72 and 74 disposed in the upper and lower clamping jaws 22 and 24, respectively. Although a drift pin is used in the illustrated embodiment, other means for maintaining proper alignment of the upper and lower clamping jaws 22 and 24 are known to and practicable in the present invention by one of ordinary skill in the art. For example, a clamping piston having an angular or irregular cross-section, such as a square, hexagon, oval, etc., may be used. Such a cross-sectional configuration of the clamping piston can maintain the upper and lower clamping jaws in a proper relationship and obviate the need for a drift pin.

The clamping piston 60 is fixed to the retractor assembly 18 (see FIG. 5) using a screw fastener 80 received in a threaded bore 82 in the top face of the upper piston section 62. The lower piston section 64 has a secondary cam passage 86 through it. The secondary cam passage 86 is alignable with the cam shaft passage 86 as well as the cam shaft passage 42. The cam shaft 40 had a cam section 44 (see FIG. 4D), which encompasses the secondary passage 86 when the cam shaft 40 is retained in the shaft passage 42. Rotating the cam shaft 40 causes the cam section 44 to engage the interior surface of the secondary cam passage 86, and to draw the lower clamping jaw 24 against the upper jaw 22, thereby setting the jaws together and fixing the rotational position of the retractor assembly 18 to the mount assembly 14.

Figure 5:
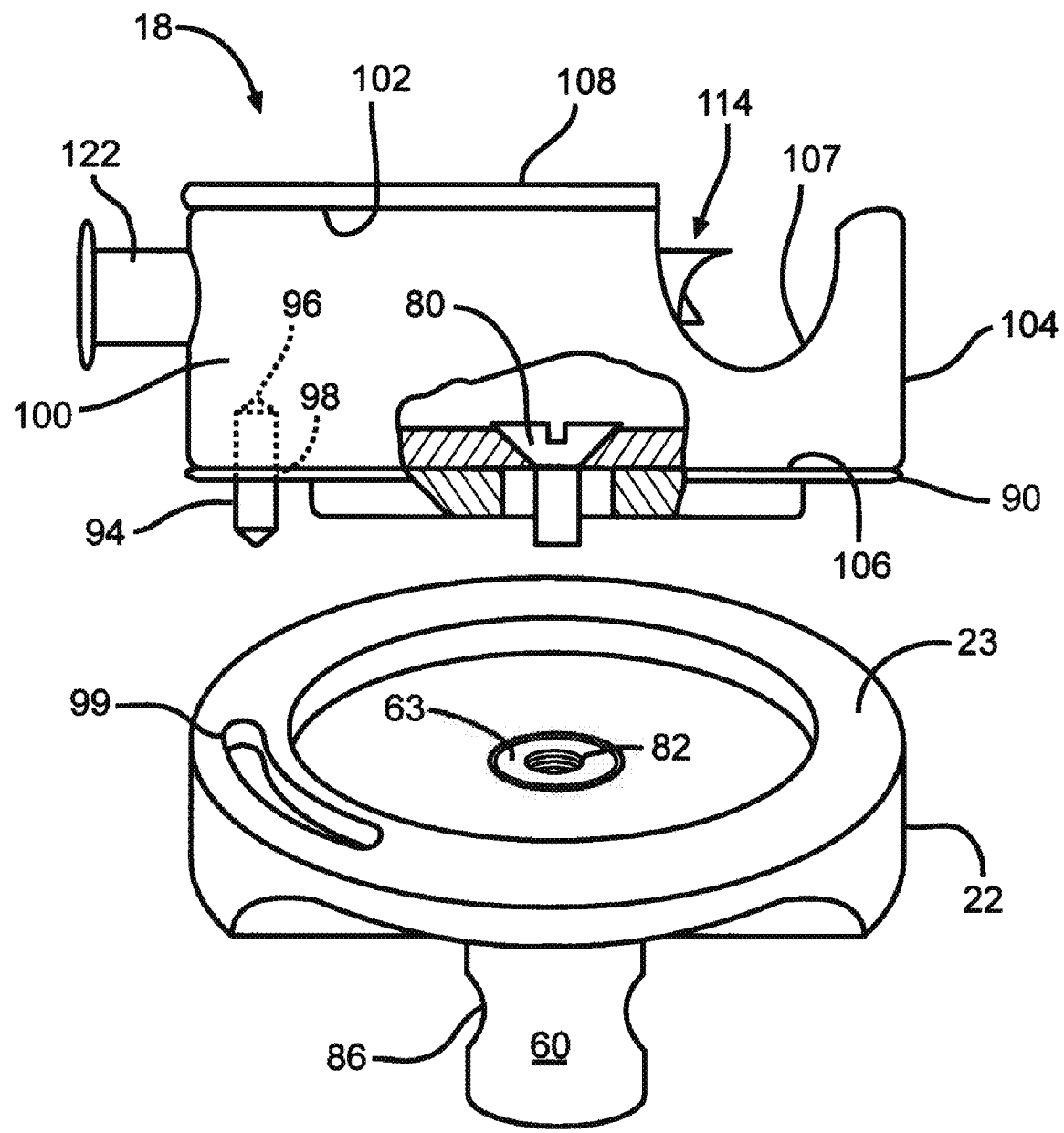
FIG. 5 is a partial cut-away side view showing an attachment means of the upper top-loading retractor section of the present invention to the lower mount section.

As illustrated in FIG. 5, the clamping piston 60 passes through a swivel plate 90 as it contacts the retractor assembly 18. The swivel plate 90 separates the retractor assembly 18 from the mount assembly 14. The top surface 63 of the upper piston section 62 has a threaded piston bore 82 set into it, thereby allowing the clamping piston 60 to be fixed to the retractor assembly 18 with a threaded fastener (swivel plate screw) 80. A swivel drift pin 94 is set into swivel drift socket 96 of the housing block 100 of the retractor assembly 18, and passes through a swivel drift hole 98 in the swivel plate 90. When the mount assembly 14 is attached to the retractor assembly 18, the swivel drift pin 94 is received in a corresponding swivel channel 99 disposed in the top surface 23 of the upper clamping jaw 22. This combination provided for limiting the degree of rotation of the retractor assembly 18 relative to the mount assembly 14 by the degrees of arc the swivel channel 99 allows the swivel drift pin 94 to travel.

Figure 2A:
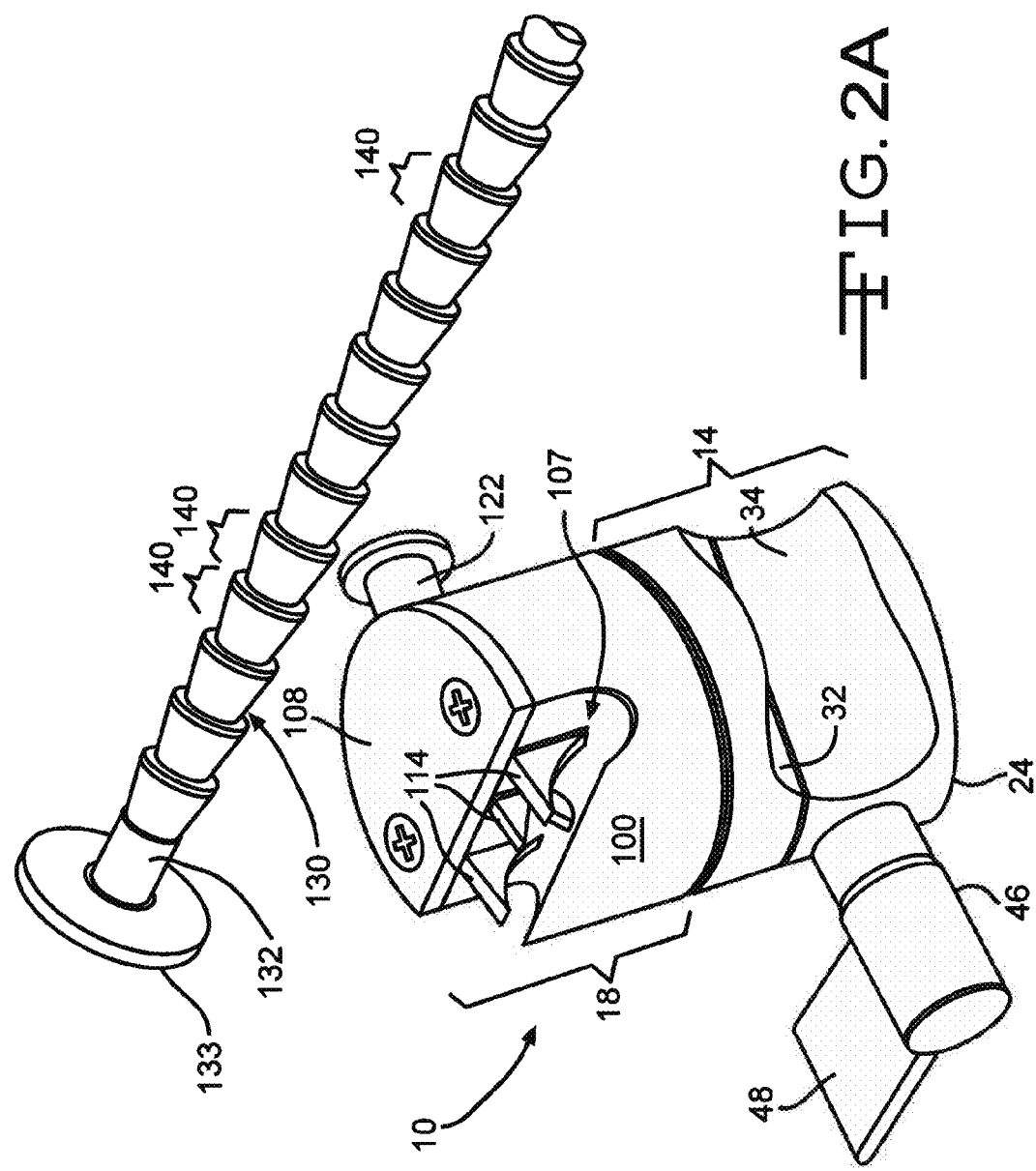
FIG. 2A and 2B are photographic views of the present combination mount and top-loading tool retractor assembly with its retractor arm (A) disengaged from the retractor mechanism and (B) engaged in the retractor mechanism.
Figure 2B:
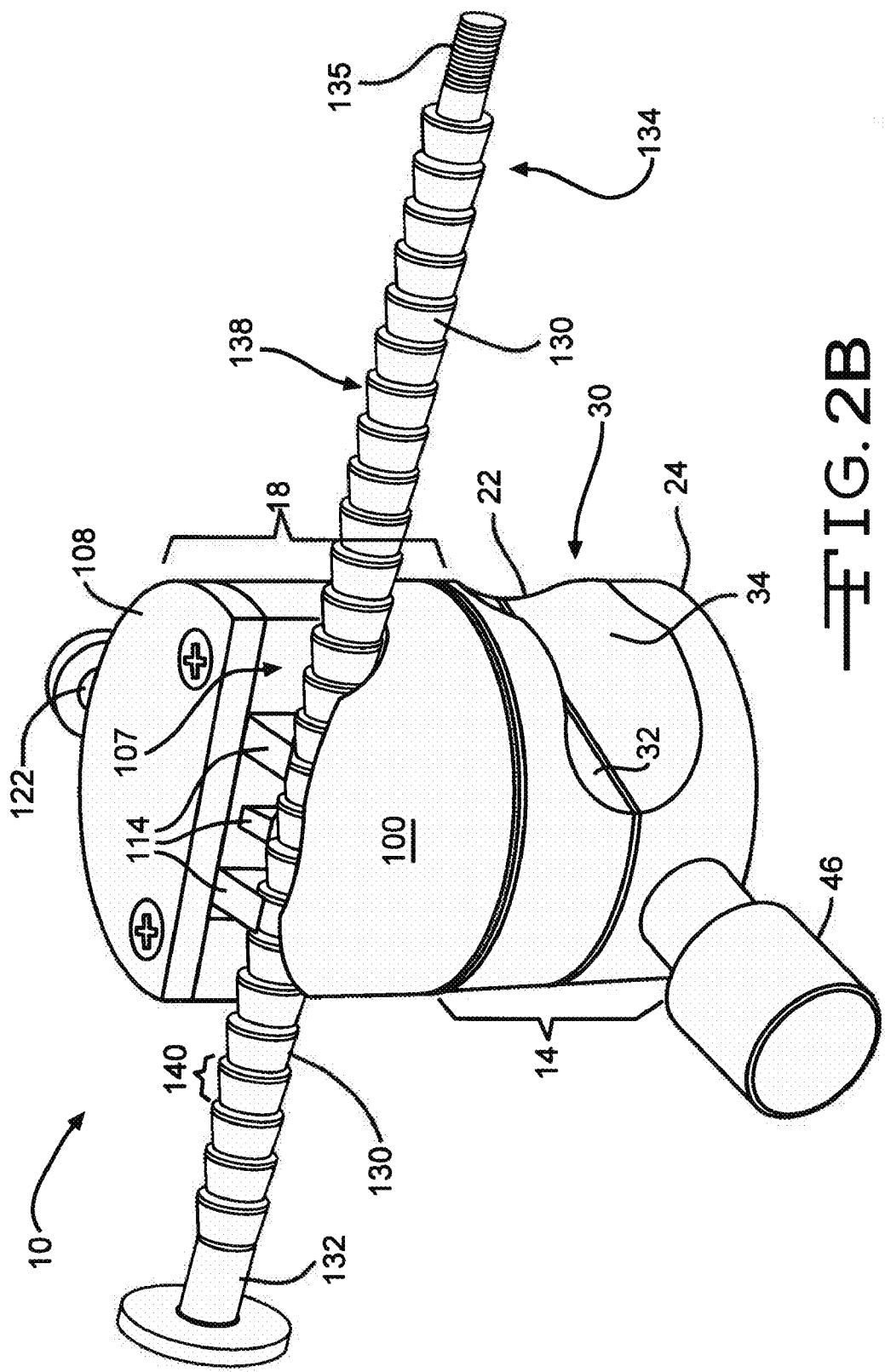

As illustrated in FIG. 5, the retractor assembly 18 comprises a housing block 100 having .a top surface 102, a side surface 104 and a bottom surface 106. A retractor mechanism 110 (see FIG. 6B) is disposed in the housing block 100 from the top surface 102. A removable cover plate 108 covers part of the top surface 102 of the housing block 100. As illustrated in FIGS. 2A and 2B, a separate retractor arm 130 is receivable into a top-loading arm slot 107 set into the uncovered portion of the top surface 102. When received therein, the retractor arm 130 is engageable by the retractor mechanism 110. The retractor arm 130 has a length extending beyond the side surfaces 104 of the housing block 100 (see FIGS. 2A and 2B), and when engaged by the retractor mechanism 110, the arm 130 is engageable at different positions along its length by the retractor mechanism 110. The retractor arm 130 has a grip end 132 to which a grip means 133 is fixed to facilitate a user positioning the arm 130 along its length in the retractor mechanism 110. An attachment fitting 135 is disposed at the distal tool end 134 of the retractor arm 130. The attachment fitting 135 allows the arm 130 to receive an adaptor 140 (see FIG. 7A), and to be attachable to a variety of surgical retractor tools. The retractor arm 130 has a ratchet surface 138 that allows it to be engaged incrementally along its length by the retractor mechanism 110. In the embodiment illustrated in FIGS. 2A and 2B, the ratchet surface 138 is configured as a unidirectional series of truncated cones 140 placed end to end. The cone features 140 of the ratchet surface 138 mate with tines 114 on an engagement fork 112 of the retractor mechanism 110.

The retractor mechanism 110 of a preferred embodiment is illustrated in FIGS. 6A and 6B. The housing block 100 has a fork recess 120 in which the engagement fork 112 is slidably received. The engagement fork 112 has two integral tines 114a and a non-integral center tine 114b. The engagement fork 112 is slidable in the fork recess 120 against a bias force. The bias force normally holds the tines 114 of the engagement fork 112 against a retractor arm 130 received in the top-loading arm slot 107. In the preferred embodiment illustrated, the bias biasing force is provided by a spring 116 disposed between the engagement fork 112 and the back wall 121 of the fork recess 120. A plunger shaft 122 passes through a plunger bore 123 through the side surface 104 and the back wall 121 of the housing block 100. The plunger shaft 122 has a tine end 124 and a plunger end 125. The tine end 124 also passes through the fork bore 113 of the engagement fork 112 to provide the non-integral center tine 114b. The plunger shaft 122 is fixed to the engagement fork 112 by a fork pin 115 inserted through a first fork pin bore 126 in the engagement fork 112, and a second fork pin bore 127 in the tine end 124 of the plunger shaft 122. When the cover plate 108 is installed on the housing 100, the fork pin 115 is held in place by the cover plate 108 blocking one end of the first fork pin bore 126 However, other means for retaining the fork pin 115 in the fork pin bore 1226 (e.g., by press fitting the pin 115 into the bore 126) are known to and practicable in the present invention by the ordinary skilled artisan.

The bias spring 116 is installed around the plunger shaft 122 inside the housing 100, as illustrated in FIG. 63. However, two bias springs 116 held in place by the cover plate 108 could be placed on either side of the plunger shaft 122 to provide the biasing force. The pitch or distance between the tines 114 compliments the pitch of the ratchet surface 138 features of the retractor arm 130.

The plunger end 125 of the plunger shaft 122 extends from the plunger bore 123 beyond the side wall 104 of the housing block 100. The plunger end 125 of the plunger shaft 122 terminates in a finger grip 128, which facilitates manual operation of the retractor mechanism 110. In using the retractor mechanism 110, the plunger end 125 of the plunger shaft 122 is manually withdrawn from the housing block 100, against the normal bias of the spring 116. Withdrawing the plunger shaft 122 draws the tines 114 of the engagement fork 112 away from the top-loading arm slot 107. This allows for insertion or removal of the retractor arm 130 into and from the top-loading arm slot 107. With the retractor arm 130 residing in the slot 107, the tines 114 of the retractor mechanism 110 impinge against and engage the ratchet surface 138 of the arm 130 to hold it in place. However, the biasing force provided by the spring 116 to hold the retractor engagement fork 112 against the arm 130 is selected so that, while providing sufficient force to hold the arm 130 in place, the force is not so great as to prevent a user from pulling on the grip end 132 of the arm 130 to draw it through the retractor mechanism 110. The ratchet surface 138 features of the retractor arm 130 and the configuration of the fork tines 114 together prevent the arm 130 from being displaced along its length in the direction opposite the grip end 132.

The cover plate 108 is fixed to the housing block 100 in any of a number of manners selectable by the ordinary skilled artisan, but in the preferred embodiment illustrated, is attached by cover screw fasteners 118 passing through cover screw holes 109 in the cover plate 108 and into threaded cover screw receptacles 101 on the housing block 100. The mountable, top-loading surgical retractor device 10 of the present invention is easily disassembled to allow the device 10 to be cleaned and sterilized. The present device 10 is composed of materials that are compatible with its use in a surgical setting and the need for its sterilization.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A surgical retractor device, comprising:
   a) a mount assembly having opposed upper and lower clamping jaws disposed to receive and grip a mounting rod;
   b) a clamping mechanism comprising a cam shaft rotatably retained in a cam shaft passage by a shaft pin disposed in the lower clamping jaw a lever, wherein the shaft pin rides in a stop channel in the cam shaft, the stop channel corresponding to rotational movement less than 360° of the cam shaft in the cam shaft passage such that the clamping mechanism provides for selectively moving the upper and lower clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;
   c) a retractor assembly pivotably supported on the upper clamping jaw of the mount assembly, the retractor assembly comprising:
      i) a housing having a top surface, a side surface, a bottom surface, and a slot comprising an open channel extending into the top surface and meeting with opposed open ends at the housing side surface; and
      ii) a retractor mechanism in the retractor assembly housing; and
   d) wherein a rod receivable in the slot of the retractor assembly housing is releasably engageable by the retractor mechanism to thereby adjust a portion of a rod's length extending beyond the retractor assembly housing.

2. The surgical retractor device of claim 1 wherein the mount assembly further comprises the opposed upper and lower clamping jaws, each having complementary portions that provide for receiving and gripping a mounting rod when the cam shaft is actuated to move the upper and lower clamping jaws into the closely spaced relationship.

3. The surgical retractor device of claim 1 wherein the retractor assembly further comprises the housing having a cross-sectional width similar to the upper and lower clamping jaws.

4. The surgical retractor device of claim 1 wherein the mount assembly and the retractor assembly are pivotable about a common axis.

5. The surgical retractor device of claim 1 wherein the mount assembly and the retractor assembly are pivotable about a common axis with a limited degree of rotation of from about 30 degrees to 200 degrees.

6. The surgical retractor device of claim 1 wherein operation of the clamping mechanism provides for setting the clamping jaws and locking the pivotable relationship of the retractor assembly relative to the mount assembly.

7. The surgical retractor device of claim 1 wherein the shaft pin rides in the stop channel in an outer circumference of the cam shaft.

8. The surgical retractor device of claim 1 wherein a clamping piston passes through upper and lower piston bores disposed in the respective upper and lower clamping jaws to thereby link the clamping jaws together.

9. The surgical retractor device of claim 1 wherein a clamping piston passes through upper and lower piston bores disposed in the respective upper and lower clamping jaws to thereby link the clamping jaws together, the clamping piston comprising an upper piston section residing in the upper piston bore with a smaller cross-section than a lower piston section residing in the lower piston bore.

10. The surgical retractor device of claim 9 further comprising:
the lower piston section of the clamping piston having a secondary cam passage alignable with the cam shaft passage disposed in the lower clamping jaw, thereby permitting the cam shaft to pass through the cam shaft passage and the secondary cam passage of the clamping piston.

11. The surgical retractor device of claim 2 wherein the mount assembly further comprises a drift pin received in corresponding drift holes in the upper and lower clamping jaws, the drift pin and drift holes in combination disposed to keep the complementary portions of the opposed upper and lower clamping jaws of the mount assembly in proper alignment with each other.

12. The surgical retractor device of claim 1 wherein a swivel drift pin is received in a swivel drift socket in the housing retractor assembly and in a corresponding swivel channel disposed in a top surface of the upper clamping jaw, the degree of rotation of the retractor assembly relative to the mount assembly being limited by the degrees of arc the swivel channel allows the swivel drift pin to travel.

13. The surgical retractor device of claim 1 wherein a rod has a grip end and a distal tool end, the grip end terminating in a grip means to facilitate a user manually positioning a rod along its length in the retractor mechanism, and a distal tool end terminating in an attachment fitting for attachment to a surgical retractor tool.

14. The surgical retractor device of claim 1 wherein the retractor mechanism is incrementally engageable with a ratchet surface of a rod.

15. The surgical retractor device of claim 1 wherein the retractor mechanism is disposed in a fork recess in the retractor assembly housing and comprises an engagement fork slidably received in the fork recess against a biasing force that biases tines of the engagement fork into the slot.

16. The surgical retractor device of claim 15 wherein the biasing force is provided by a spring disposed between the engagement fork and a back wall of the fork recess.

17. The surgical retractor device of claim 16 wherein the retractor mechanism further comprising a plunger shaft having a tine end attached to the engagement fork and a plunger end passing through a plunger bore in the back wall of the fork recess and extending beyond the side surface of the retractor assembly housing to facilitate manual operation of the retractor mechanism.

18. The surgical retractor device of claim 1 wherein the retractor mechanism is retained in the retractor assembly housing block by a cover plate removably attached to the top surface thereof.

19. The surgical retractor device of claim 1 wherein the cam shaft has a lever attached to a shaft end extending from the shaft passage external to the lower clamping jaw, the lever enabling a user to apply a force to rotate the cam shaft in the shaft passage.

20. The surgical retractor device of claim 8 wherein the clamping piston is fixed to the retractor assembly housing at an upper piston section.

21. The surgical retractor device of claim 9 wherein the cam shaft has an eccentric cam section disposed in the secondary cam passage so that rotational movement of the cam shaft causes the eccentric cam section to engage an interior surface of the secondary cam passage and draw the lower clamping jaw against the upper jaw, thereby moving the clamping jaws together and fixing the rotational position of the retractor assembly relative to the mount assembly.

22. The surgical retractor device of claim 14 wherein the ratchet surface comprises a unidirectional series of truncated cone features that are matable with tines on an engagement fork of the retractor mechanism.

23. The surgical retractor device of claim 17 wherein the plunger end of the plunger shaft extending beyond the side surface of the retractor assembly housing terminates in a finger grip.

24. A surgical retractor device, comprising:
a) a mount assembly having opposed upper and lower clamping jaws disposed to receive and grip a mounting rod;
b) a clamping mechanism comprising a cam shaft rotatably retained in a cam shaft passage by a shaft pin disposed in the lower clamping jaw, wherein the shaft pin rides in a stop channel in the cam shaft, the stop channel corresponding to rotational movement less than 360° of the cam shaft in the cam shaft passage such that the clamping mechanism provides for selectively moving the upper and lower clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;
c) a retractor assembly pivotably supported on the upper clamping jaw of the mount assembly, the retractor assembly comprising:
   i) a housing having a top surface, a side surface, a bottom surface, and a slot comprising an open channel extending from at least the top surface and meeting with opposed open ends at the housing side surface; and
   ii) a retractor mechanism in the retractor assembly housing; and
d) wherein a clamping piston passes through upper and lower piston bores disposed in the respective upper and lower clamping jaws to thereby link the clamping jaws together, the clamping piston comprising an upper piston section residing in the upper piston bore with a smaller cross-section than a lower piston section residing in the lower piston bore;

e) wherein the lower piston section of the clamping piston has a secondary cam passage alignable with the cam shaft passage, thereby permitting the cam shaft to be rotatably retained in the cam shaft passage and in the secondary cam passage of the clamping piston, and wherein the cam shaft has an eccentric cam section disposed in the secondary cam passage so that rotational movement of the cam shaft causes the eccentric cam section to engage an interior surface of the secondary cam passage and draw the lower clamping jaw against the upper jaw, thereby moving the clamping jaws together and fixing the rotational position of the retractor assembly relative to the mount assembly; and f) wherein a rod receivable in the slot of the retractor assembly housing is releasably engageable by the retractor mechanism to thereby adjust a portion of a rod's length extending beyond the retractor assembly housing.

25. A surgical retractor device, comprising:
a) a mount assembly having opposed upper and lower clamping jaws disposed to receive and grip a mounting rod;
b) a clamping mechanism comprising a cam shaft rotatably retained in a cam shaft passage by a shaft pin disposed in the lower clamping jaw, wherein the shaft pin rides in a stop channel in the cam shaft, the stop channel corresponding to rotational movement less than 360° of the cam shaft in the cam shaft passage such that the clamping mechanism provides for selectively moving the upper and lower clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;
c) a retractor assembly pivotably supported on the upper clamping jaw of the mount assembly, the retractor assembly comprising a housing having a top surface, a side surface, a bottom surface, and a slot comprising an open channel extending into the top surface and meeting with opposed open ends at the housing side surface;
d) a retractor mechanism disposed in a fork recess in the retractor assembly housing, the retractor mechanism comprising:
   i) an engagement fork slidably received in the fork recess against a spring disposed between the engagement fork and a back wall of the fork recess to bias tines of the engagement fork into the arm slot; and
   ii) a plunger shaft having a tine end attached to the engagement fork with a plunger end passing through a plunger bore in the back wall of the fork recess and extending beyond the side surface of the retractor assembly housing to facilitate manual operation of the retractor mechanism; and
e) wherein a rod receivable in the slot of the retractor assembly housing is releasably engageable by the retractor mechanism to thereby adjust a portion of a rod's length extending beyond the retractor assembly housing.

26. The surgical retractor device of claim 24 wherein the mount assembly and the retractor assembly are pivotable about a common axis with a limited degree of rotation of from about 30 degrees to 200 degrees.

27. The surgical retractor device of claim 25 wherein operation of the clamping mechanism provides for setting the clamping jaws and locking the pivotable relationship of the retractor assembly relative to the mount assembly.

28. A surgical retractor device, comprising:
a) a mount assembly having opposed upper and lower clamping jaws disposed to receive and grip a mounting rod;
b) a clamping mechanism comprising a cam shaft rotatably received in a cam shaft passage disposed in the lower clamping jaw, the clamping mechanism providing for selectively moving the upper and lower clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;
c) a clamping piston passes through upper and lower piston bores disposed in the respective upper and lower clamping jaws to thereby link the clamping jaws together;
d) a retractor assembly pivotably supported on the upper clamping jaw of the mount assembly, the retractor assembly comprising:
   i) a housing having a top surface, a side surface, a bottom surface, and a slot comprising an open channel extending into the top surface and meeting with opposed open ends at the housing side surface; and
   ii) a retractor mechanism in the retractor assembly housing; and
e) wherein the clamping piston disposed in the upper and lower clamping jaws is fixed to the retractor assembly housing at an upper piston section; and
f) wherein a rod receivable in the slot of the retractor assembly housing is releasably engageable by the retractor mechanism to thereby adjust a portion of a rod's length extending beyond the retractor assembly housing.

29. The surgical retractor device of claim 28 wherein the mount assembly and the retractor assembly are pivotable about a common axis with a limited degree of rotation of from about 30 degrees to 200 degrees.

30. A surgical retractor device, comprising:
a) a mount assembly having opposed upper and lower clamping jaws disposed to receive and grip a mounting rod;
b) a clamping mechanism comprising a lever, the clamping mechanism providing for selectively moving the upper and lower clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;
c) a retractor assembly pivotably supported on the upper clamping jaw of the mount assembly, the retractor assembly comprising:
   i) a housing having a top surface, a side surface, a bottom surface, and a slot comprising an open channel extending into the top surface and meeting with opposed open ends at the housing side surface; and ii) a retractor mechanism in the retractor assembly housing, wherein tines on an engagement fork of the retractor mechanism are incrementally engageable with a ratchet surface comprising a unidirectional series of truncated cone features of the retractor mechanism of a rod to thereby advance the fork along the rod upon manipulation of the fork; and d) wherein a rod receivable in the slot of the retractor assembly housing is releasably engageable by the retractor mechanism to thereby adjust a portion of a rod's length extending beyond the retractor assembly housing.

31. The surgical retractor device of claim 30 wherein the mount assembly and the retractor assembly are pivotable about a common axis with a limited degree of rotation of from about 30 degrees to 200 degrees.

32. A surgical retractor device, comprising:

a) a mount assembly having opposed first and second clamping jaws disposed to receive and grip a mounting rod;

b) a clamping mechanism comprising a cam shaft rotatably retained in a cam shaft passage by a shaft pin disposed in the first clamping jaw, wherein the shaft pin rides in a stop channel in the cam shaft, the stop channel corresponding to rotational movement less than 360° of the cam shaft in the cam shaft passage such that the clamping mechanism provides for selectively moving the first and second clamping jaws into and out of a closely spaced relationship, wherein when the cam shaft is actuated to move the clamping jaws into a closely spaced relationship, the mount assembly is capable of gripping a mounting rod received therein and when the cam shaft is actuated to move the clamping jaws into a relatively spaced apart relationship, they are releasable from a mounting rod to allow for repositioning of the clamping mechanism comprising the retractor device along a length of a mounting rod;

c) a retractor assembly pivotably supported on one of the first and the second clamping jaws of the mount assembly, the retractor assembly comprising:

i) a housing having a top surface, a side surface, a bottom surface, and a slot comprising an open channel extending into the top surface and meeting with opposed open ends at the housing side surface; and ii) a retractor mechanism in the retractor assembly housing; and d) wherein a rod receivable in the slot of the retractor assembly housing is releasably engageable by the retractor mechanism to thereby adjust a portion of a rod's length extending beyond the retractor assembly housing.

33. The surgical retractor device of claim 32 wherein the mount assembly and the retractor assembly are pivotable about a common axis with a limited degree of rotation of from about 30 degrees to 200 degrees.

* * * * *

UNITED STATES PATENT AND TRADEMARK OFFICE
CERTIFICATE OF CORRECTION

| | | |
|---|---|---|
| PATENT NO. | : 7,887,481 B2 | |
| APPLICATION NO. | : 11/381153 | |
| DATED | : February 15, 2011 | |
| INVENTOR(S) | : Thomas Lamadon | |

It is certified that error appears in the above-identified patent and that said Letters Patent is hereby corrected as shown below:

Column 6, line 24 - delete "a lever"

Signed and Sealed this
Nineteenth Day of April, 2011

David J. Kappos
*Director of the United States Patent and Trademark Office*